United States Patent
Pees et al.

(10) Patent No.: US 7,084,146 B2
(45) Date of Patent: Aug. 1, 2006

(54) FUNGICIDAL TRIFLUOROMETHYLALKYLAMINO-TRIAZOLOPYRIMIDINES

(75) Inventors: Klaus-Juergen Pees, Mainz (DE); Guenter Krummel, Vendersheim (DE); Henry Van Tuyl Cotter, Trenton, NJ (US); Guido Albert, Hackenheim (DE); Annerose Rehnig, Ingelheim (DE); Leslie May, Wokingham (GB); Waldemar Pfrengle, Seibersbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 264 days.

(21) Appl. No.: 09/840,488

(22) Filed: Apr. 23, 2001

(65) Prior Publication Data

US 2003/0055069 A1    Mar. 20, 2003

Related U.S. Application Data

(62) Division of application No. 09/272,916, filed on Mar. 19, 1999, now Pat. No. 6,255,309.

(51) Int. Cl.
C07D 487/04    (2006.01)
A01N 43/90    (2006.01)

(52) U.S. Cl. .................. 514/259.31; 544/263
(58) Field of Classification Search ........... 514/259.31; 544/263
See application file for complete search history.

(56) References Cited

U.S. PATENT DOCUMENTS

| | | | |
|---|---|---|---|
| 5,593,996 A | | 1/1997 | Pees et al. |
| 5,948,783 A | * | 9/1999 | Pees et al. .............. 544/263 |
| 5,981,534 A | * | 11/1999 | Pfrengle .................. 514/183 |
| 6,204,269 B1 | * | 3/2001 | Pfrengle et al. ...... 514/259.31 |
| 6,255,309 B1 | * | 7/2001 | Pees et al. .............. 544/263 |
| 6,284,762 B1 | * | 9/2001 | Pfrengle ................. 544/263 |
| 2002/0068744 A1 | * | 6/2002 | Schmitt et al. ....... 514/259.31 |
| 2004/0097522 A1 | * | 5/2004 | Gebauer et al. ...... 514/259.31 |
| 2004/0110771 A1 | * | 6/2004 | Blasco et al. ......... 514/259.31 |
| 2004/0127509 A1 | * | 7/2004 | Blasco et al. ......... 514/259.31 |
| 2004/0162286 A1 | * | 8/2004 | Blasco et al. ........... 514/227.8 |
| 2004/0167136 A1 | * | 8/2004 | Blasco et al. ......... 514/259.31 |
| 2005/0090508 A1 | * | 4/2005 | Zhang et al. ......... 514/259.31 |
| 2005/0124635 A1 | * | 6/2005 | Wu et al. .............. 514/259.31 |

FOREIGN PATENT DOCUMENTS

JP    2000086412    *    3/2000

* cited by examiner

*Primary Examiner*—Mark L. Berch
(74) *Attorney, Agent, or Firm*—Novak Druce DeLuca & Quigg

(57) ABSTRACT

The novel compounds of formula I:

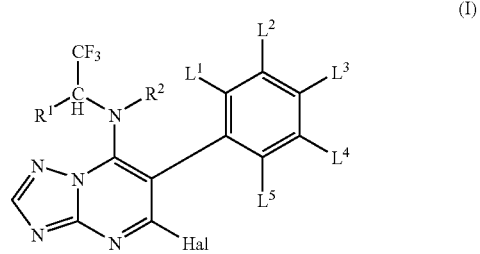

wherein
$R^1$ is hydrogen or methyl;
$R^2$ is hydrogen, or an optionally substituted alkyl, alkenyl, alkynyl, alkadienyl or phenyl group;
Hal is halogen; and
$L^1$ through $L^5$ are each hydrogen, halogen, alkyl, alkoxy or nitro, provided that at least one of $L^1$ through $L^5$ represents nitro or alkoxy;
show selective fungicidal activity. The new compounds are processed with carriers and adjuvants to fungicidal compositions.

9 Claims, No Drawings

FUNGICIDAL TRIFLUOROMETHYLALKYLAMINO-TRIAZOLOPYRIMIDINES

This is a divisional application of application Ser. No. 09/272,916 filed on Mar. 19, 1999 (now U.S. Pat. No. 6,255,309), the entire disclosure of which is hereby incorporated by reference, which claims priority under 35 USC §119 of PCT/US 98/05615, filed on Mar. 23, 1998, which claims the benefit of U.S. Provisional Application No. 60/043,820, filed Apr. 14, 1997.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0 071 792 claims compounds of the formula

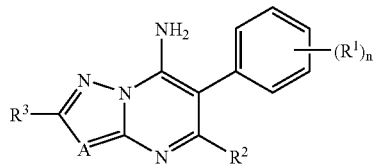

in which $R^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi.

EP 0 550 113-A2 claims compounds of the formula

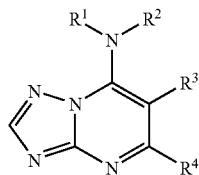

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. Thus, compounds in which $R^1$ is a trifluoromethylalkyl group are generally embraced by this patent application. However, there is no single compound disclosed in which $R^1$ is a trifluoromethylalkyl group.

SUMMARY OF THE INVENTION

The present invention provides a compound of formula I

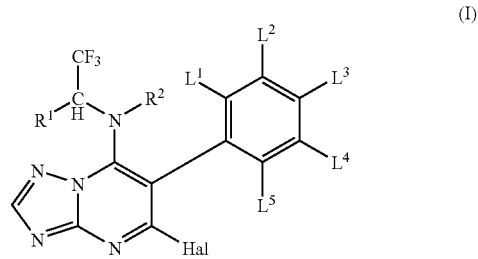

in which
$R^1$ represents a hydrogen or a methyl group;
$R^2$ represents a hydrogen atom or an optionally substituted alkyl, alkenyl, alkynyl, alkadienyl or phenyl group;
Hal represents a halogen atom; and
$L^1$ through $L^5$ each independently represent an hydrogen or halogen atom or an alkyl, alkoxy or nitro group, provided that at least one of $L^1$ through $L^1$ represents a nitro or alkoxy group.

The new compounds show excellent selective fungicidal activity in various crops.

It is an object of the present invention to provide novel, selective fungicidal compounds.

It is also an object of the invention to provide methods for controlling undesired fungus by contacting said plants with a fungicidally effective amount of the new compounds.

It is another object of the invention to provide selective fungicidal compositions containing the new compounds as active ingredients.

These as well as further objects and features of the invention will be more apparent from the detailed description set forth herein below, and from the appended claims.

DETAILED DESCRIPTION OF THE PREFERRED EMBODIMENTS

It has surprisingly been found that the novel compounds of formula I

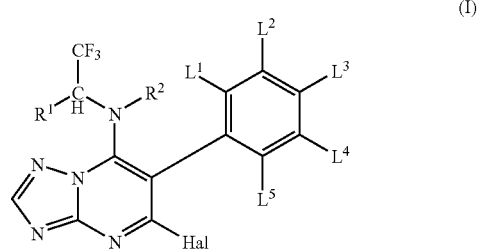

in which $R^1$, $R^2$, Hal and $L^1$ through $L^5$ have the meaning given above for formula I show excellent fungicidal activity against a broad range of fungi.

Unless otherwise stated, as used herein the term halogen atom may denote a bromine, iodine, chlorine or fluorine atom, and is especially a bromine, chlorine or fluorine atom. Hal preferably represents a chlorine atom.

Optionally substituted moieties may be unsubstituted or have from one up to the maximal possible number of substituents. Typically, 0 to 3 substituents are present.

Unless otherwise stated herein, the terms alkyl, alkenyl, alkynyl, alkadienyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkenyl moiety has from 2 to 6 carbon atoms. A preferred alkenyl moiety is allyl or especially a 2-methylallyl group.

The invention especially relates to compounds of formula I in which any alkyl part of the groups $R^1$ and/or $R^2$ which may be straight chained or branched, contains up to 10 carbon atoms, preferably up to 9 carbon atoms, more preferably up to 6 carbon atoms, any alkenyl or alkynyl part of the substituents $R^1$ and/or $R^2$ contains up to 10 carbon atoms, preferably up to 9 carbon atoms, more preferably up to 6 carbon atoms, and in which each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, trialkylsilyl, preferably tri-$C_{1-4}$ alkylsilyl, phenyl, halo- or dihalo-phenyl or pyridyl groups. Any alkyl, alkenyl or alkynyl group may be linear or branched. A halogen atom suitably denotes a fluorine, chlorine or bromine atom.

The invention especially relates to compounds of formula I, in which $R^1$ represents a hydrogen atom, a $C_{1-10}$ alkyl or a phenyl group, in particular a hydrogen atom or a methyl group.

Included in the scope of the present invention are (R) and (S) isomers and atropisomers of compounds of formula I, which have a chiral center or in which the substituents $L^1$ or $L^1$ and $L^2$ are different from $L^5$ or $L^5$ and $L^4$, and the racemates thereof, and salts, N-oxides and acid addition compounds.

Particularly interesting activity has been found in (S)-isomer compounds of formula I wherein the group —CH(CF$^3$)$R^1$ is chiral.

Another preferred embodiment of the present invention are the compounds of formula I, wherein $R^2$ represents a hydrogen atom or a $C_{1-10}$ alkyl group or a $C_{3-10}$ alkenyl group.

Those compounds of formula I in which at least one of $R^1$ and $R^2$ represents a hydrogen atom are particularly preferred.

The compounds according to formula I may be oils, gums, or, predominantly crystalline solid materials. They exhibit valuable fungicidal properties, especially enhanced systemicity and enhanced fungicitoxity against rice diseases and powdery mildews compared to conventional fungicides known in the art. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis,* Helmintho-sporium tritici repentis, *Leptosphaeria nodorum, Micronectriella nivalis, Monilinia fructigena, Mycosphaerella ligulicola, Mycosphaerella pinodes, Pyricularia grisea* f.sp. *oryzae, Rhizoctonia solani, Venturia inaequalis, Uncinula necator* and *Sclerotinia sclerotiorum*, in particular for the control of *Uncinula necator, Pyricularia grisea* f.sp. *oryzae* and *Rhizoctonia solani*. The compounds of formula I according to the invention possess a high fungicidal activity within a wide concentration range and may be used in agriculture without significant difficulties.

Moreover, the compounds according to the invention show enhanced residual control of fungi, in particular of grape powdery mildew compared with conventional fungicides.

Good control of phythopathogenic fungi may be obtained with a compound as defined in formula I wherein:
at least one of $L^1$ and $L^5$ represents a halogen atom; and/or
$R^1$ represents a hydrogen atom or a methyl group.

Especially good results in terms of control of phytopathogenic fungi are obtained by using, for example, the following compounds of formula I:
5-chloro-6-(4-methoxyphenyl)-7-(2,2,2-trifluoroethylamino)-[1,2,4]triazolo[1,5-a]pyrimidine, 5-chloro-6-(4-nitrophenyl)-7-(2,2,2-trifluoroethylamino)-[1,2,4]triazolo[1,5-a]pyrimidine, and 5-chloro-6-(2,6-difluoro4-methoxyphenyl)-7-[2-(1,1,1-trifluoro)propylamino]-[1,2,4]triazolo[1,5-a]pyrimidine.

The present invention further provides a process for the preparation of a compound of formula I as defined above which comprises
treating a compound of formula II

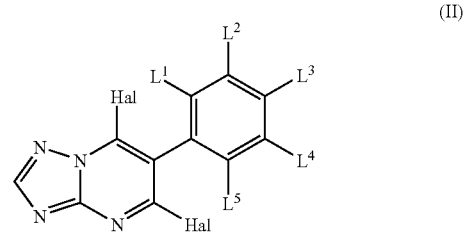

(II)

in which
$L^1$ through $L^5$ and Hal are as defined in any one of the preceding claims;
with an amine or amide of formula III

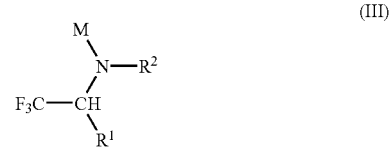

(III)

in which
$R^1$ and $R^2$ are as defined hereinbefore,
M represents a hydrogen atom or an equivalent of a free or complexed metal atom, preferably selected from the group consisting of Li, Na, K, Zn and Cu, to produce a compound of formula I.

Compounds of formula II are known e.g. from EP 0 550 113 and are conventionally prepared by reacting 3-amino-1,2,4-triazole with 2-phenyl-substituted malonic acid ester of formula IV,

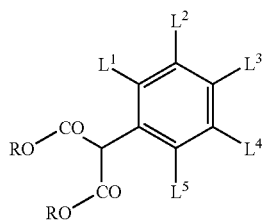

(IV)

wherein

R represents alkyl, under alkaline conditions, preferably using high boiling tertiary amines as for example tri-n-butylamine.

The resulting 5,7-dihydroxy-6-phenyltriazolopyrimidines are subsequently treated with a halogenating agent, preferably with a brominating or chlorinating agent, such as phosphorus oxybromide or phosphorus oxychloride, neat or in the presence of a solvent. The reaction is suitably carried out at a temperature in the range from 0° C. to 150° C., the preferred reaction temperature being from 80° C. to 125° C.

The reaction between the 5,7-dihalo-6-phenyltriazolopyrimidines of formula II and the amine or amide of formula III is conveniently carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The compounds according to the invention may also be obtained by reacting a 7-amino-5-halo-6-phenyltriazolopyrimidine with a trifluoroalkanoic acid or a reactive derivative thereof, in particular with trifluoroacetic acid anhydride, in the presence of a base and subsequent reduction of the resulting trifluoroalkanoic amide.

The amines of formula III, wherein M represents a hydrogen atom, are well-known in the literature or commercially available or may be prepared analogously to methods that are known per se. The amides of formula III, wherein M represents a metal atom are, as a rule, obtained from the corresponding amines (M=hydrogen) by reaction with an alkyl lithium compound optionally followed by a transmetallation reaction.

Due to excellent activity, the compounds of formula I may be used in cultivation of all plants where infection by phytopathogenic fungi is not desired, e.g. cereals, solanaceous crops, vegetables, legumes, apples, vine.

The invention further provides a fungicidal composition which comprises an active ingredient, which is at least one compound of formula I as defined above, and one or more carriers. A method of making such a composition is also provided, which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into, e.g., emulsion concentrates, solutions, oil in water emulsions, wettable powders, soluble powders, suspension concentrates, dusts, granules, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso®200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to formula I to be formulated. Surfactants may also mean mixtures of individual surfactants.

The compositions of the invention may for example be formulated as wettable powders, water dispersible granules, dusts, granules, tablets, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention include:

| Emulsion Concentrate (EC) | | |
|---|---|---|
| Active Ingredient | Compound of Example 8 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Sheilsol ® A[2] (mixture of $C_9$—$C_{10}$ aromatic hydrocarbons) | to 1000 ml |
| Suspension Concentrate (SC) | | |
| Active Ingredient | Compound of Example 8 | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound of Example 8 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |
| Water Dispersible Granules (WG) | | |
| Active Ingredient | Compound of Example 8 | 50% (w/w) |
| Dispersing/Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of formula I alone. Furthermore, the other pesticide can have a synergistic effect on the pesticidal activity of the formula I compound.

The other fungicidal compound can be, for example, one which is also capable of combating diseases of cereals (e.g. wheat) such as those caused by i Erysipha, Puccinia, Septoria, Gibberella and *Helminthosporium* spp., seed and soil borne diseases and downy and powdery mildews on vines, early and late blight on solanaceous crops, and powdery mildew and scab on apples etc. These mixtures of fungicides can have a broader spectrum of activity than the compound of formula I alone. Furthermore, the other fungicide can have a synergistic effect on the fungicidal activities of the compound of formula I.

Examples of the other fungicidal compounds are anilazine, azoxystrobin, benalaxyl, benomyl, bethoxazin, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram In addition, the co-formulations according to the invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verticillium lecanii, Autographica californica NPV, Beauvaria bassiana, Ampelomyces quisqualis, Bacilis subtilis, Pseudomonas chlororaphis, Pseudomonas fluorescens, Steptomyces griseoviridis* and *Trichoderma harzianum.*

Moreover, the co-formulations according to the invention may contain at least one compound of formula I and a chemical agent that induces the systemic acquired resistance in plants such as for example nicotinic acid or derivatives thereof or BION.

The compounds of formula I can be mixed with soil, peat or other rooting media for the protection of the plants against seed-borne, soil-borne or foliar fungal diseases.

The invention still further provides the use as a fungicide of a compound of the formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

5-Chloro-6-(4-methoxyphenyl)-7-N-(2,2,2-trifluoro-ethylamino)-1,2,4-triazolo[1.5a]pyrimidine A mixture of 2,2,2-trifluoroethylamine (4.2 mmoles) and dichloromethane (10 ml) is added to a mixture of 5,7-dichloro-6-(4-methoxyphenyl)-1,2,4-triazolo[1.5a]pyrimidine (1.4 mmoles) and dichloromethane (30 ml) under stirring. The reaction mixture is stirred 16 hours at room temperature, subsequently washed two times with 1 N hydrochloric acid and once with water. The organic layer is separated, dried with anhydrous sodium sulfate and the solvent is evaporated under reduced pressure. Treatment of the resulting light brown oil with tert.-butyl methyl ether (50 ml) yields beige crystals having a melting point of 183–185° C.

EXAMPLES 2–3

The following examples (Table I; structure and melting point) are synthesized analogously to Example 1.

| Example | $R^1$ | $R^2$ | $L^1$ | $L^2$ | $L^3$ | $L^4$ | $L^5$ | melting point (° C.) |
|---|---|---|---|---|---|---|---|---|
| 2 | H | H | H | H | $NO_2$ | H | H | 237 |
| 3 | H | H | F | H | $OCH_3$ | H | F | oil |

What is claimed is:

1. A compound of formula I

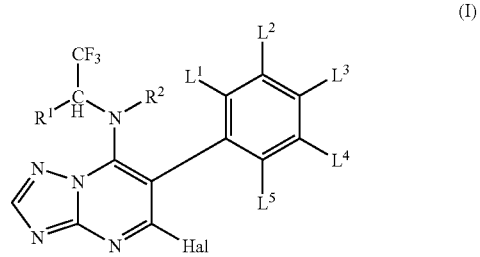

in which

R¹ represents a hydrogen or a methyl group;

R² represents a hydrogen atom or an optionally substituted $C_1$–$C_{10}$-alkyl, $C_2$–$C_{10}$-alkenyl, $C_2$–$C_{10}$-alkynyl, $C_4$–$C_{10}$-alkadienyl or phenyl group, wherein the optional substituents are selected from the group consisting of nitro, cyano, $C_3$–$C_6$-cycloalkyl; $C_3$–$C_6$-cycloalkenyl, $C_1$–$C_6$-haloalkyl, $C_3$–$C_6$-halocycloalkyl, $C_1$–$C_6$-alkoxy, $C_1$–$C_6$-haloalkoxy, tri-$C_1$–$C_4$-alkylsilyl, phenyl, halophenyl, dihalophenyl and pyridyl;

Hal represents a halogen atom and

L¹ through L⁵ each represent a hydrogen or halogen atom or an $C_1$–$C_{10}$-alkyl, $C_1$–$C_{10}$-alkoxy or nitro group, provided that at least one of L¹ through L⁵ represents a nitro or alkoxy group.

2. A compound according to claim 1 in which at least one of L¹ and L⁵ represents a halogen atom.

3. A compound according to claim 1 in which R² represents a hydrogen or a $C_{1-10}$ alkyl group.

4. A compound according to claim 1 in which at least one of R² and R² represents a hydrogen atom.

5. The compound of formula I defined in claim 1 which is selected from the group consisting of 5-chloro-6-(4-methoxyphenyl)-7-(2,2,2-trifluoroethylamino)-[1,2,-4]triazolo[1,5-a]pyrimidine;

5-chloro-6-(4-nitrophenyl)-7-(2,2,2-trifluoroethylamino)-[1,2,4]-triazolo[1,5-a]pyrimidine; and 5-chloro-6-(2,6-difluoro-4-methoxyphenyl)-7-[2-(1,1,1-trifluoro)-propyl)amino]-[1,2,4]triazolo[1,5-a]pyrimidine.

6. A process for the preparation of a compound of formula I as defined in claim 1, which process comprises:

treating a compound of formula II

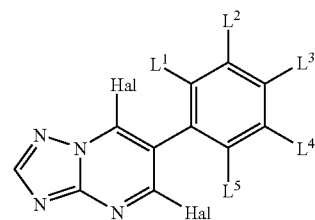

(II)

with an amine of formula III

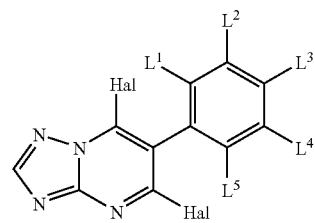

(II)

in which M represents a hydrogen atom or a metal atom, to produce the compound of formula I.

7. A fungicidal composition which comprises a carrier, and as active agent, at least one compound of formula I as defined in claim 1.

8. A method of combating fungus at a locus which comprises treating the locus with a fungicidally effective amount of a compound of formula I as defined in claim 1.

9. The process of claim 6 wherein the metal atom represented by M is selected from the group consisting of Li, Na, K and Cu.

* * * * *

UNITED STATES PATENT AND TRADEMARK OFFICE
CERTIFICATE OF CORRECTION

PATENT NO. : 7,084,146 B2  Page 1 of 1
APPLICATION NO. : 09/840488
DATED : August 1, 2006
INVENTOR(S) : Pees et al.

It is certified that error appears in the above-identified patent and that said Letters Patent is hereby corrected as shown below:

Column 12, indicated lines 15 – 25:

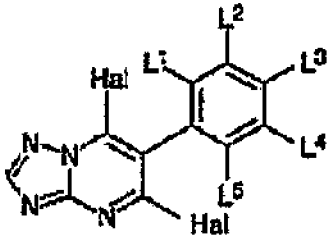   (II)

should be

   (III)

Signed and Sealed this

Seventeenth Day of April, 2007

JON W. DUDAS
*Director of the United States Patent and Trademark Office*